(12) United States Patent
Lai et al.

(10) Patent No.: US 7,691,917 B2
(45) Date of Patent: Apr. 6, 2010

(54) SILCONE-CONTAINING PREPOLYMERS

(75) Inventors: Yu-Chin Lai, Pittsford, NY (US); Weihong Lang, Amston, CT (US); Edmond T. Quinn, Rochester, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 474 days.

(21) Appl. No.: 11/762,970

(22) Filed: Jun. 14, 2007

(65) Prior Publication Data

US 2008/0312397 A1 Dec. 18, 2008

(51) Int. Cl.
G02B 1/04 (2006.01)
C08F 290/06 (2006.01)
C08G 77/04 (2006.01)
C08G 77/20 (2006.01)

(52) U.S. Cl. .......... 523/106; 523/107; 528/26; 528/27; 528/33; 528/35

(58) Field of Classification Search .......... 528/26, 528/27, 33, 35; 523/106, 107
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 3,808,179 A | 4/1974 | Gaylord | |
| 4,005,024 A | 1/1977 | Rodriguez et al. | |
| 4,006,176 A | 2/1977 | Heckert et al. | |
| 4,113,224 A | 9/1978 | Clark et al. | |
| 4,153,641 A | 5/1979 | Deichart et al. | |
| 4,185,087 A | 1/1980 | Morlino | |
| 4,189,546 A | 2/1980 | Deichert et al. | |
| 4,197,266 A | 4/1980 | Clark et al. | |
| 4,259,467 A | 3/1981 | Keogh et al. | |
| 4,260,725 A | 4/1981 | Keogh et al. | |
| 4,321,261 A | 3/1982 | Ellis et al. | |
| 4,388,229 A | 6/1983 | Fu | |
| 4,418,165 A | 11/1983 | Polmanteer et al. | |
| 4,472,327 A | 9/1984 | Neefe | |
| 4,486,577 A * | 12/1984 | Mueller et al. | 525/474 |
| 4,495,361 A | 1/1985 | Friends et al. | |
| 4,533,714 A | 8/1985 | Sebag et al. | |
| 4,555,732 A | 11/1985 | Tuhro | |
| 4,605,712 A * | 8/1986 | Mueller et al. | 525/474 |
| 4,633,003 A | 12/1986 | Falcetta et al. | |
| 4,640,941 A | 2/1987 | Park et al. | |
| 4,686,267 A | 8/1987 | Ellis et al. | |
| 4,745,142 A | 5/1988 | Ohwaki et al. | |
| 4,833,225 A | 5/1989 | Schaefer et al. | |
| 4,871,530 A | 10/1989 | Grollier et al. | |
| 4,891,166 A * | 1/1990 | Schaefer et al. | 554/39 |
| 4,910,277 A | 3/1990 | Bambury et al. | |
| 5,006,622 A | 4/1991 | Kunzler et al. | |
| 5,008,613 A | 4/1991 | Steinel et al. | |
| 5,013,459 A | 5/1991 | Gettings et al. | |
| 5,034,461 A | 7/1991 | Lai et al. | |
| 5,039,458 A | 8/1991 | Braatz et al. | |
| 5,070,170 A | 12/1991 | Robertson et al. | |
| 5,070,215 A | 12/1991 | Bambury et al. | |
| 5,128,408 A | 7/1992 | Tanaka et al. | |
| 5,137,448 A | 8/1992 | Dougherty et al. | |
| 5,246,607 A | 9/1993 | Schaefer et al. | |
| 5,260,000 A | 11/1993 | Nandu et al. | |
| 5,271,875 A | 12/1993 | Appleton et al. | |
| 5,271,876 A | 12/1993 | Ibar | |
| 5,321,108 A | 6/1994 | Künzler et al. | |
| 5,328,685 A * | 7/1994 | Janchitraponvej et al. | 424/70.11 |
| 5,340,583 A | 8/1994 | Dziabo et al. | |
| 5,358,995 A | 10/1994 | Lai et al. | |
| 5,359,104 A | 10/1994 | Higgs et al. | |
| 5,374,662 A | 12/1994 | Lai et al. | |
| 5,387,105 A | 2/1995 | Dougherty et al. | |
| 5,387,662 A | 2/1995 | Künzler et al. | |
| 5,393,330 A | 2/1995 | Chen et al. | |
| 5,420,324 A | 5/1995 | Lai et al. | |
| 5,451,617 A | 9/1995 | Lai et al. | |
| 5,451,651 A | 9/1995 | Lai | |
| 5,496,871 A | 3/1996 | Lai et al. | |
| 5,515,117 A | 5/1996 | Dziabo et al. | |
| 5,539,016 A | 7/1996 | Künzler et al. | |
| 5,594,085 A | 1/1997 | Lai | |
| 5,610,252 A | 3/1997 | Bambury et al. | |
| 5,639,908 A | 6/1997 | Lai | |

(Continued)

FOREIGN PATENT DOCUMENTS

EP 0 017 121 1/1983

(Continued)

OTHER PUBLICATIONS

Benjamin, William J., Oxygen Permeability (Dk) of Thirty-Seven Rigid Contact Lens Materials, Optometry and Vision Science, vol. 79, No. 2, Feb. 2002, pp. 103-111.

*Primary Examiner*—Randy Gulakowski
*Assistant Examiner*—Robert Loewe
(74) *Attorney, Agent, or Firm*—John E. Thomas

(57) ABSTRACT

Prepolymers comprising at least one block of Formula II and terminated with a polymerizable ethylenically unsaturated radical are useful in hydrogel materials are disclosed:

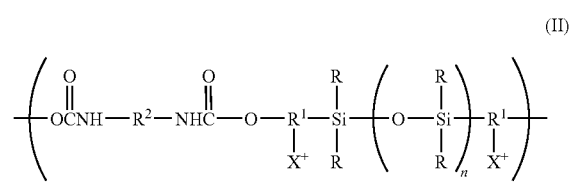

(II)

wherein n, R, $R^1$, $R^2$ and $X^+$ are as defined herein.

52 Claims, No Drawings

U.S. PATENT DOCUMENTS

| | | | |
|---|---|---|---|
| 5,648,515 A | 7/1997 | Lai | |
| 5,707,434 A | 1/1998 | Halloran et al. | |
| 5,710,302 A | 1/1998 | Kunzler et al. | |
| 5,714,557 A | 2/1998 | Kunzler et al. | |
| 5,725,736 A | 3/1998 | Schroeder et al. | |
| 5,776,999 A | 7/1998 | Nicolson et al. | |
| 5,807,956 A | 9/1998 | Czech | |
| 5,830,546 A | 11/1998 | Ehret et al. | |
| 5,844,026 A | 12/1998 | Galbo et al. | |
| 5,882,687 A | 3/1999 | Park et al. | |
| 5,908,906 A | 6/1999 | Kunzler et al. | |
| 5,962,548 A | 10/1999 | Vanderlaan et al. | |
| 5,994,488 A | 11/1999 | Yokota et al. | |
| 6,013,711 A | 1/2000 | Lewis et al. | |
| 6,022,836 A | 2/2000 | Dubief et al. | |
| 6,063,888 A | 5/2000 | Yamaguchi et al. | |
| 6,068,929 A | 5/2000 | Dauth et al. | |
| 6,132,705 A | 10/2000 | Schehlmann et al. | |
| 6,136,304 A * | 10/2000 | Pyles | 424/70.28 |
| 6,166,236 A | 12/2000 | Bambury et al. | |
| 6,242,554 B1 | 6/2001 | Busch et al. | |
| 6,248,803 B1 | 6/2001 | Nakanishi et al. | |
| 6,258,367 B1 * | 7/2001 | Dupuis | 424/401 |
| 6,346,594 B1 * | 2/2002 | Watanabe et al. | 528/26 |
| 6,482,969 B1 | 11/2002 | Helmrick et al. | |
| 6,528,465 B1 | 3/2003 | Cantoro | |
| 6,534,184 B2 | 3/2003 | Knasiak et al. | |
| 6,607,717 B1 | 8/2003 | Johnson et al. | |
| 6,613,755 B2 | 9/2003 | Peterson et al. | |
| 6,630,132 B2 | 10/2003 | Fender et al. | |
| 6,649,722 B2 | 11/2003 | Rosenzweig et al. | |
| 6,706,680 B2 | 3/2004 | Fender et al. | |
| 6,730,767 B2 | 5/2004 | Salamone et al. | |
| 6,733,123 B2 * | 5/2004 | Polzhofer et al. | 351/160 H |
| 6,787,603 B2 | 9/2004 | Johnson et al. | |
| 6,815,074 B2 | 11/2004 | Aguado et al. | |
| 6,822,016 B2 | 11/2004 | McCabe et al. | |
| 6,849,671 B2 | 2/2005 | Steffen et al. | |
| 6,849,755 B2 | 2/2005 | Ozai et al. | |
| 6,852,793 B2 | 2/2005 | Salamone et al. | |
| 6,867,172 B2 | 3/2005 | Alvarez et al. | |
| 6,893,595 B1 | 5/2005 | Muir et al. | |
| 6,951,894 B1 | 10/2005 | Nicolson et al. | |
| 2002/0082312 A1 * | 6/2002 | Lai | 522/36 |
| 2002/0107337 A1 * | 8/2002 | Rosenzweig et al. | 525/474 |
| 2004/0029981 A1 | 2/2004 | Herzig et al. | |
| 2004/0116310 A1 * | 6/2004 | Kunzler et al. | 510/115 |
| 2004/0120914 A1 * | 6/2004 | Decoster et al. | 424/70.12 |
| 2005/0008613 A1 | 1/2005 | Peterson et al. | |
| 2005/0171232 A1 | 8/2005 | Ford et al. | |
| 2006/0072069 A1 * | 4/2006 | Laredo et al. | 351/160 H |
| 2006/0074208 A1 * | 4/2006 | Laredo | 526/279 |
| 2007/0264503 A1 * | 11/2007 | Lai et al. | 428/411.1 |

FOREIGN PATENT DOCUMENTS

| | | |
|---|---|---|
| EP | 0 396 364 | 6/1997 |
| EP | 0 837 103 | 4/1998 |
| EP | 0 837 104 | 4/1998 |
| JP | 9183813 | 7/1997 |

* cited by examiner

SILICONE-CONTAINING PREPOLYMERS

BACKGROUND OF THE INVENTION

1. Technical Field

The present invention generally relates to polysiloxane prepolymers and their use as biomedical devices such as ophthalmic lenses.

2. Description of Related Art

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply exclusively from contact with the atmosphere, good oxygen permeability is a critical characteristic for any contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

Hydrogels represent a desirable class of materials for many biomedical applications, including contact lenses and intraocular lenses. Hydrogels are hydrated, cross-linked polymeric systems that contain water in an equilibrium state. Silicone hydrogels are a known class of hydrogels and are characterized by the inclusion of a silicone-containing material. Typically, a silicone-containing monomer is copolymerized by free radical polymerization with a hydrophilic monomer, with either the silicone-containing monomer or the hydrophilic monomer functioning as a crosslinking agent (a crosslinker being defined as a monomer having multiple polymerizable functionalities) or a separate crosslinker may be employed. An advantage of silicone hydrogels over non-silicone hydrogels is that the silicone hydrogels typically have higher oxygen permeability due to the inclusion of the silicone-containing monomer. Because such hydrogels are based on monomers polymerizable by free radical, these materials are thermosetting polymers.

U.S. Pat. No. 5,034,461 discloses neutral polyurethane-containing prepolymers. These prepolymers may be copolymerized with a hydrophilic comonomer to form a silicone hydrogel copolymer that is useful as a contact lens material and other biomedical device applications. The prepolymers exemplified in U.S. Pat. No. 5,034,461 do not include any major hydrophilic portion, and therefore, these prepolymers are copolymerized with a hydrophilic monomer to form a hydrogel copolymer.

It would be desirable to provide improved biomedical devices formed from silicone-containing material that exhibit suitable physical and chemical properties, e.g., oxygen permeability and wettability, for prolonged contact with the body while also being biocompatible.

SUMMARY OF THE INVENTION

In accordance with one embodiment of the present invention, a prepolymer comprising at least one block of Formula II and terminated with a polymerizable ethylenically unsaturated radical:

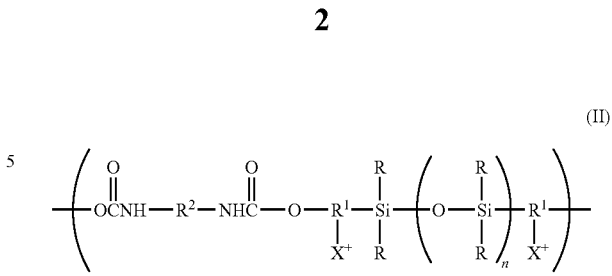

wherein n, R, $R^1$, $R^2$ and $X^+$ are as defined herein.

In accordance with a second embodiment of the present invention, a copolymer is provided comprising a polymerization product of a monomeric mixture comprising one or more prepolymers comprising at least one block of Formula II and terminated with a polymerizable ethylenically unsaturated radical:

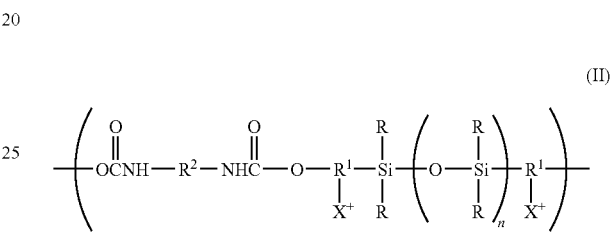

wherein n, R, $R^1$, $R^2$ and $X^+$ are as defined herein.

In accordance with a third embodiment of the present invention, a biomedical device is provided comprising a polymerization product of a monomeric mixture comprising one or more prepolymers comprising at least one block of Formula II and terminated with a polymerizable ethylenically unsaturated radical:

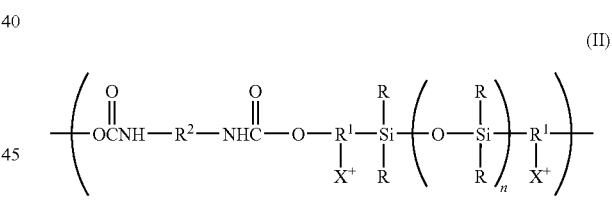

wherein n, R, $R^1$, $R^2$ and $X^+$ are as defined herein.

In accordance with a fourth embodiment of the present invention, a prepolymer of Formula IV is provided:

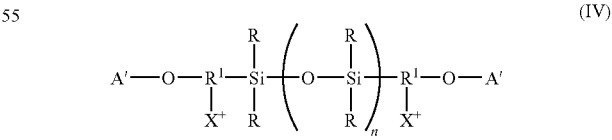

wherein n, R, $R^1$, $X^+$ and A' are as defined herein.

In accordance with a fifth embodiment of the present invention, a copolymer is provided comprising a polymerization product of a monomeric mixture comprising one or more prepolymers of Formula IV:

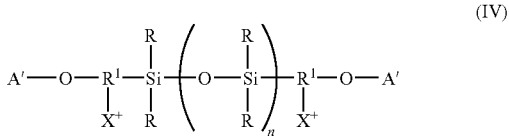

wherein n, R, $R^1$, $X^+$ and A' are as defined herein.

In accordance with a sixth embodiment of the present invention, a biomedical device is provided comprising a copolymer comprising a polymerization product of a monomeric mixture comprising one or more prepolymers of Formula IV:

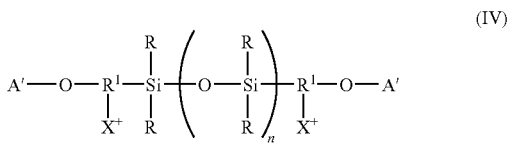

wherein n, R, $R^1$, $X^+$ and A' are as defined herein.

The prepolymers and copolymer of the present invention advantageously provide improved biomedical devices exhibiting a combination of oxygen permeability, surface wettability and physical strength in dry and/or hydrated forms otherwise unavailable.

DETAILED DESCRIPTION OF THE PREFERRED EMBODIMENTS

The present invention is directed to prepolymers and copolymers useful as biomedical devices intended for direct contact with body tissue or fluid. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. A wide variety of types of contact lens materials can be produced herein ranging from hard, gas permeable lens materials; soft, hydrogel lens materials to soft, non-hydrogel lens materials. A particularly preferred contact lens is a soft, hydrogel lens.

In one embodiment, a prepolymer of the present invention is a prepolymer having at least one block of Formula II and terminated with a polymerizable ethylenically unsaturated radical:

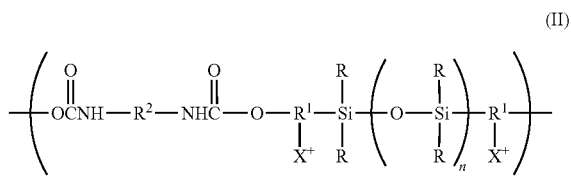

wherein n is at least 1, preferably from 10 to 100 and more preferably from 20 to 70; R is independently a monovalent hydrocarbon radical having 1 to 30 carbon atoms which may include ether linkages therebetween including, by way of example, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, and a substituted or unsubstituted $C_5$-$C_{30}$ arylalkyl group; a halogen substituted monovalent hydrocarbon radical having 1 to about 20 carbon atoms which may include ether linkages therebetween including, by way of example, a $C_1$-$C_{30}$ fluoro-substituted alkyl group or alkenyl group; a $C_1$-$C_{20}$ ester group; an ether or polyether-containing group, e.g., an alkyl ether, cycloalkyl ether, cycloalkylalkyl ether, cycloalkenyl ether, aryl ether, arylalkyl ether, polyalkyl ether, polycycloalkyl ether, polycycloalkylalkyl ether, polycycloalkenyl ether, polyaryl ether or polyarylalkyl ether; an ureido group; an amide group; an amine group; a substituted or unsubstituted $C_1$-$C_{30}$ alkoxy group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; fluorine; a vinyl group; a $C_5$-$C_{30}$ fluoroaryl group and combinations thereof; $R^1$ is independently a substituted or unsubstituted divalent hydrocarbon radical having 1 to 30 carbon atoms which may include ether linkages therebetween including, by way of example, a substituted or unsubstituted $C_1$-$C_{30}$ alkylene, substituted or unsubstituted $C_3$-$C_{30}$ cycloalkylene, and substituted or unsubstituted $C_5$-$C_{30}$ arylene radical, substituted radicals of the foregoing in which some of the hydrogen atoms are substituted with halogen atoms, and combinations thereof; $X^+$ is independently a cationic-containing group and $R^2$ is a diradical residue of a diisocyanate.

Representative examples of alkyl groups for use herein include, by way of example, a straight or branched hydrocarbon chain radical containing carbon and hydrogen atoms of from 1 to about 30 carbon atoms with or without unsaturation, to the rest of the molecule, e.g., methyl, ethyl, n-propyl, 1-methylethyl (isopropyl), n-butyl, n-pentyl, etc., and the like.

Representative examples of fluoroalkyl groups for use herein include, by way of example, a straight or branched alkyl group as defined herein having one or more fluorine atoms attached to the carbon atom, e.g., —$CF_3$, —$CF_2CF_3$, —$CH_2CF_3$, —$CH_2CF_2H$, —$CF_2H$ and the like.

Representative examples of cycloalkyl groups for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronaphthyl, adamantyl and norbornyl groups bridged cyclic group or spirirobicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of fluoroaryl groups for use herein include, by way of example, an aryl group as defined herein having one or more fluorine atoms attached to the aryl group.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$(R^3OR^4)_t$, wherein $R^3$ is a bond, a substituted or unsubstituted alkyl, cycloalkyl or aryl group as defined herein and $R^4$ is a substituted or unsubstituted alkyl, cycloalkyl or aryl group as defined herein and t is at least 1, e.g., —$CH_2CH_2OC_6H_5$ and $CH_2$—$CH_2$—$CH_2$—O—$CH_2$—$(CF_2)_z$—H where z is 1 to 6, —$CH_2CH_2OC_2H_5$, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of amide groups for use herein include, by way of example, an amide of the general formula —$R^5C(O)NR^6R^7$ wherein $R^5$, $R^6$ and $R^7$ are independently $C_1$-$C_{30}$ hydrocarbons, e.g., —$R^5$ can be alkylene groups, arylene groups, cycloalkylene groups and $R^6$ and $R^7$ can be alkyl groups, aryl groups, and cycloalkyl groups as defined herein and the like.

Representative examples of amine groups for use herein include, by way of example, an amine of the general formula —$R^8NR^9R^{10}$ wherein $R^8$ is a $C_2$-$C_{30}$ alkylene, arylene, or cycloalkylene and $R^9$ and $R^{10}$ are independently $C_1$-$C_{30}$ hydrocarbons such as, for example, alkyl groups, aryl groups, or cycloalkyl groups as defined herein.

Representative examples of alkoxy groups for use herein include, by way of example, an alkyl group as defined herein attached via oxygen linkage to the rest of the molecule, i.e., of the general formula —$OR^{11}$, wherein $R^{11}$ is an alkyl, cycloalkyl, cycloalkylalkyl, cycloalkenyl, aryl or an arylalkyl as defined herein, e.g., —$OCH_3$, —$OC_2H_5$, or —$OC_6H_5$, and the like.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocylic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined herein directly bonded to an alkyl group as defined herein. The heterocycloalkyl radical may be attached to the main structure at carbon atom in the alkyl group that results in the creation of a stable structure.

Representative examples of $X^+$ include cationic groups of the formula: —$X^1$—$N^+R^{16}_3$, —$X^1$—$P^+R^{17}_3$, —$X^1$—$S^+R^{17}_2$, or —$X^1$-Het$^+$, wherein $X^1$ is a substituted or unsubstituted alkylene group of 1 to about 12 carbon atoms, substituted or unsubstituted arylene group, substituted or unsubstituted alkylene arylene group, substituted or unsubstituted arylene alkylene group, substituted or unsubstituted alkylene aryl alkylene group, substituted or unsubstituted cycloalkylene group, substituted or unsubstituted alkylene cycloalkyl group, substituted or unsubstituted cycloalkyl alkylene group or substituted or unsubstituted alkylene cycloalkyl alkylene group; $R^{16}$ independently is hydrogen or a substituted or unsubstituted alkyl group of 1 to 4 carbon atoms, preferably methyl, or substituted or unsubstituted aryl, such as substituted or unsubstituted phenyl, or two of the $R^{16}$ groups together with the nitrogen atom to which they are attached form an aliphatic heterocyclic ring containing from 5 to 7 atoms, or three $R^{16}$ groups together with the nitrogen atom to which they are attached form a fused ring structure containing from 5 to 7 atoms in each ring; $R^{17}$ independently is $R^{16}$ or a group —$OR^6$, wherein $R^{16}$ is as defined herein; or Het is an aromatic nitrogen-, phosphorus- or sulphur-, preferably nitrogen-, containing ring such as, for example, pyridine.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring', 'substituted carboxylic acid derivative', substituted alkylene, substituted disubstituted-arylene, substituted alkylene arylene, substituted arylene alkylene, substituted alkylene aryl alkylene, substituted cycloalkylene, substituted alkylene cycloalkyl, substituted cycloalkyl alkylene and substituted alkylene cycloalkyl alkylene may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —$COOR_x$, —$C(O)R_x$, —$C(S)R^x$, —$C(O)NR_xR_y$, —$C(O)ONR_xR_y$, —$NR_xCON$-$R_yR_z$, —$N(R_x)SOR_y$, —$N(R_x)SO_2R_y$, —(=N—$N(R_x)R_y$), —$NR_xC(O)OR_y$, —$NR^x,R_y$, —$NR_xC(O)R_y$—, —$NR_xC(S)$ $R_y$—$NR_xC(S)NR_yR^z$, —$SONR_xR_y$—, —$SO_2NR_xR_y$—, —$OR_x$, —$ORC(O)NR_xR_z$, —$OR_xC(O)OR_y$—, —$OC(O)R_x$, —$OC(O)NR_xR_y$, —$R_xNR_yC(O)R^z$, —$R_xOR_y$, —$R_xC(O)$ $OR_y$, —$R_xC(O)NR_yR^z$, —$R_xC(O)R^x$, —$R_xOC(O)R_y$, —$SR_x$, —$SOR_x$, —$SO_2R_x$, —$ONO_2$, wherein $R_x$, $R_y$ and $R_z$ in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

The prepolymers are endcapped on at least one end and preferably both ends with a polymerizable ethylenically unsaturated radical, e.g., A and A'. Representative examples of a "polymerizable ethylenically unsaturated radical" include, by way of example, (meth)acrylate-containing radicals, (meth)acrylamide-containing radicals, vinylcarbonate-containing radicals, vinylcarbamate-containing radicals, styrene-containing radicals and the like. In one embodiment, a polymerizable ethylenically unsaturated radical can be represented by the general formula:

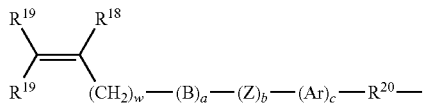

wherein
$R^{18}$ is hydrogen or methyl;
each $R^{19}$ is independently hydrogen, an alkyl radical having 1 to 6 carbon atoms, or a —CO—Y—$R^{21}$ radical wherein Y is —O—, —S— or —NH— and $R^{21}$ is an alkyl radical having 1 to about 10 carbon atoms;
$R^{20}$ is a divalent alkenyl radical having 1 to about 12 carbon atoms;
B denotes —O— or —NH—; Z denotes —CO—, —OCO— or —COO;
Ar denotes an aromatic radical having 6 to about 30 carbon atoms;
w is 0 to 6; a is 0 or 1; b is 0 or 1; and c is 0 or 1.

Suitable endcapping precursors, for forming the polymerizable ethylenically unsaturated radicals include, by way of example, hydroxy-terminated (meth)acrylates, such as 2-hydroxyethylmethacrylate, 2-hydroxyethylacrylate, and 3-hydroxypropylmethacrylate; and amino-terminated (meth) acrylates, such as t-butylaminoethylmethacrylate and aminoethylmethacrylate; and (meth)acrylic acid, especially where the polymeric precursor is end capped with diisocyanate. Suitable end capping precursors for forming the polymerizable ethylenically unsaturated radicals can also include, for example, isocyanate-terminated (meth) acrylates, such as 2-isocyanato ethyl methacrylate, especially where the polymeric precursor is end capped with a hydroxyl. As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid.

In another embodiment, a prepolymer of the present invention can be represented by general Formula III:

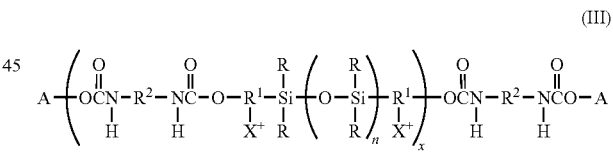

wherein n, R, $R^1$, $R^2$ and $X^+$ have the aforestated meanings; x is an integer from 1 to 20 and preferably from 1 to 10 and more preferably from 2 to about 6 and each A is independently a polymerizable ethylenically unsaturated radical as defined herein.

Generally, the prepolymers of this invention can be prepared by first reacting a cationic diol-terminated siloxane represented by general Formula I:

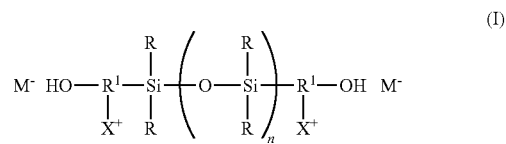

wherein n, R, R¹ and X⁺ have the aforestated meanings and M⁻ is a counter ion such as, for example, chloride, bromide, iodide and the like.

Suitable cationic diol-terminated siloxanes represented by general Formula I can be prepared by methods known in the art and are commercially available from such sources as Siltech Inc. under the tradename Silquat®, e.g., Silquat® Di-12, Silquat® Di-20, Silquat® Di-50 and the like. The compounds of Formula I can have a number average molecular weight ranging from about 700 to about 10,000 and preferably from about 1,500 to about 6,000.

Generally, any diisocyanate may be employed in forming the prepolymers of this invention. Suitable diisocyanates may be aliphatic or aromatic, and include alkyl, alkyl cycloalkyl, cycloalkyl, alkyl aromatic and aromatic diisocyanates preferably having 6 to 30 carbon atoms in the aliphatic or aromatic moiety. Specific examples of suitable diisocyanates include isophorone diisocyanate, hexamethylene-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyantomethyl)cyclohexane, and cyclohexane diisocyanate. A diisocyanate which itself can be a reaction product of a diisocyanate in excess with a short chain diol, is also useful for this invention.

Generally, the reaction of a diisocyanate with a cationic diol-terminated polysiloxane is conducted in the presence of a catalyst, such as dibutyl tin dilaurate and in a solvent, such as methylene chloride or tetrahydrofuran and under reflux. The cationic polysiloxane and diisocyanate are ordinarily added at a molar ratio less than about 1:1. As one skilled in the art will readily appreciate, the number of blocks formed for the prepolymer can be controlled by varying the molar ratio of the cationic polysiloxane to diisocyanates. Generally, in one embodiment, a molar ratio of cationic polysiloxane to diisocyanate can range from about 20:21 to about 1:2 and preferably from about 2:3 to about 9:10. The reaction of diols with diisocyanates will yield urethane radicals (—NH—COO— or —OCO—NH—).

Finally, this product is endcapped with the polymerizable ethylenically unsaturated radical.

In another embodiment, a prepolymer of the present invention can be represented by general Formula IV:

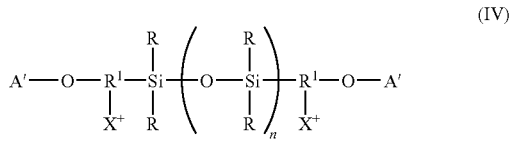

(IV)

wherein n, R, R¹ and X⁺ have the aforestated meanings and each A' is independently a polymerizable ethylenically unsaturated-containing radical as defined herein.

Generally, the prepolymers of Formula IV can be prepared by reacting a cationic diol-terminated siloxane represented by general Formula I with a suitable compound having a polymerizable ethylenically unsaturated-containing group. Representative examples of polymerizable ethylenically unsaturated-containing groups include vinyl, allyl, acryloyl, acryloyloxy, methacryloyl, methacryloyloxy, fumaryl, styryl, itaconyl, maleimido, methacrylamido, and acrylamido-containing groups, and combinations thereof. These compounds also can have one or two epoxide, isocyanate, isothiocyanate, amine, hydroxyl, thiol, acid chloride or anhydride groups. Preferred compounds having a polymerizable ethylenically unsaturated-containing groups include compounds having a acryloyl or methacryloyl group, e.g., acryloyl chloride, methacryloyl chloride and the like; compounds having an anhydride group, e.g., maleic anhydride, itaconic anhydride and the like; compounds having a fumaryl group, e.g., fumaryl chloride and the like; compounds having an itaconyl group, e.g., itaconyl chloride and the like; and compounds having an isocyanate group, e.g., isocyanatoethyl methacrylate and the like.

The reaction of a cationic diol-terminated siloxane with a compound having a polymerizable ethylenically unsaturated-containing group can be conducted in the presence of a catalyst, such as dibutyl tin dilaurate and in a solvent, such as methylene chloride, and under reflux. The cationic polysiloxane and polymerizable ethylenically unsaturated-containing group are ordinarily added at a molar ratio of cationic polysiloxane to polymerizable ethylenically unsaturated-containing group of from about 1:1 to about 1:2 and preferably about 1:2.

The copolymers of this invention are formed by copolymerizing the foregoing polysiloxane prepolymers of this invention with one or more comonomers. Since the prepolymers are endcapped with polymerizable ethylenically unsaturated radicals, they are polymerizable by free radical polymerization. The monomeric mixtures employed in the invention include conventional lens-forming or device-forming monomers. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) For copolymers, the prepolymers of this invention are included in the monomeric mixture at about 5 to about 95 weight percent, and preferably about 20 to about 70 weight percent.

At least one hydrophilic comonomer can be combined with the silicone-containing prepolymers of this invention in the initial monomeric mixture. Representative examples of hydrophilic comonomers include, but are not limited to, unsaturated carboxylic acids, such as methacrylic and acrylic acids; (meth)acrylic substituted alcohols, such as 2-hydroxyethylmethacrylate, 2-hydroxyethylacrylate and glyceryl methacrylate; vinyl lactams, such as N-vinyl pyrrolidone; and (meth)acrylamides, such as methacrylamide and N,N-dimethylacrylamide. A hydrogel is a crosslinked polymeric system that can absorb and retain water in an equilibrium state. At least one hydrophilic monomer is included in the monomer mixture at about 20 to about 60 weight percent, and preferably about 25 to about 50 weight percent.

According to various preferred embodiments, the initial monomeric mixture can comprise at least one (meth)acrylic substituted alcohol, such as at least one of 2-hydroxyethylmethacrylate and glyceryl methacrylate, preferably in an amount of at least about 1 weight percent of the monomeric mixture, and preferably in an amount of about 2 to about 10 weight percent. Preferably, the monomeric mixture further includes at least one vinyl lactam, such as N-vinyl pyrrolidone and/or at least one (meth)acrylamides, such as N,N-dimethylacrylamide.

Another class of lens-forming or device-forming monomers is silicone-containing monomers. In other words, another silicone-containing comonomer which contains from 1 to about 60 silicone atoms, in addition to the polysiloxane prepolymer of this invention, may be included in the initial monomeric mixture, for example, if it is desired to obtain a copolymer with high oxygen permeability.

One suitable class of silicone containing monomers include known bulky, monofunctional polysiloxanylalkyl monomers represented by Formula V:

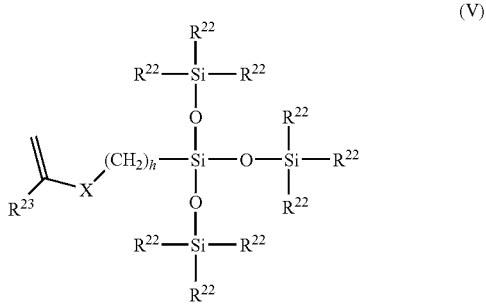

X is —COO—, —CONR$^{24}$—, —OCOO—, or —OCONR$^{24}$— wherein each R$^{24}$ is H or lower alkyl; R$^{23}$ is hydrogen or lower alkyl such as methyl; h is 1 to 10; and each R$^{22}$ independently is a lower alkyl or halogenated alkyl radical, a phenyl radical or a radical of the formula —Si(R$^{25}$)$_3$ wherein each R$^{25}$ is independently a lower alkyl radical or a phenyl radical. Such bulky monomers specifically include methacryloxypropyl tris(trimethylsiloxy)silane (TRIS), pentamethyldisiloxanyl methylmethacrylate, tris(trimethylsiloxy)methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate.

In addition to silicone monomers, hydrophobic monomers can be added to the monomeric mixtures to modify properties of hydrogels derived therefrom. The hydrophobic monomers can be added, for example, to impart mechanical enhancing properties of a hydrogel such as tear strength. This is of particular importance if certain formulations gave hydrogels with tear strength less than ideal for a certain applications such as contact lenses. Hydrophobic monomers having aliphatic ring structures are particularly useful for increasing tear strength of a hydrogels. Suitable hydrophobic monomers having aliphatic ring structures include, but are not limited to, isobornenyl acrylate, isobornenyl methacrylate, cyclohexyl methacrylate and the like.

Various difunctional and multifunctional silicone-containing monomers are known in the art and may be used as a comonomer if desired.

The monomer mixtures may include the silicone comonomer, in addition to the subject prepolymers, at 0 to about 50 weight percent, preferably about 5 to about 30 weight percent when present.

For silicone hydrogels, the monomer mixture includes a crosslinking monomer (a crosslinking monomer being defined as a monomer having multiple polymerizable functionalities). Since the prepolymers of this invention can be endcapped at both ends with a polymerizable radical, the prepolymers will function as a crosslinker. Optionally, a supplemental crosslinking monomer may be added to the initial monomeric mixture. Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a supplemental crosslinking agent is employed, this monomeric material may be included in the monomer mixture at about 0.1 to about 20 weight percent, and more preferably at about 0.2 to about 10 weight percent.

The hydrogel copolymer, when fully hydrated, has a water content of at least about 20 weight percent, as measured gravimetrically. Especially preferred are hydrogel copolymers having a water content of at least about 30 weight percent.

Also, it is preferred that the hydrogel copolymer has a tensile modulus no greater than about 100 g/mm$^2$, more preferably a modulus between about 40 and about 80 g/mm$^2$. Modulus may be measured with an Instron (Model 4502) instrument according to ASTM D-1708a, where the hydrogel copolymer film sample is immersed in borate buffered saline. An appropriate size of the film sample is gauge length 22 mm and width 4.75 mm, where the sample further has ends forming a dogbone shape to accommodate gripping of the sample with clamps of the Instron instrument, and a thickness of 200±50 microns.

It is preferred that the hydrogel copolymer have an oxygen permeability of at least about 80 barrers, more preferably at least about 110 barrers, and most preferably at least about 130 barrers.

The preferred combinations of water content and oxygen permeability may also be described as (i) a water content in the range of at least about 30 to no greater than about 60 weight percent and/or (ii) an oxygen permeability greater than about 110 barrers.

Oxygen permeability (also referred to as Dk) is determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value (R$^2$) of 0.97 or higher should be entered into the calculation of Dk value. At least two Dk measurements per thickness, and meeting R$^2$ value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., *The Oxygen Permeability of Reference Materials*, Optom V is Sci 7 (12s): 95 (1997), the disclosure of which is incorporated herein in its entirety:

In the case of intraocular lenses, the monomer mixtures may further include a monomer for increasing the refractive index of the resultant copolymer. Examples of such monomers are aromatic (meth) acrylates, such as phenyl (meth) acrylate, phenylethyl (meth)acrylate and benzyl (meth)acrylate.

An organic diluent may be included in the initial monomeric mixture. As used herein, the term "organic diluent" encompasses organic compounds that are substantially unreactive with the components in the initial mixture, and are often used to minimize incompatibility of the monomeric components in this mixture. Representative organic diluents include: monohydric alcohols, such as $C_2$-$C_{10}$ monohydric alcohols; diols such as ethylene glycol; polyols such as glycerin; ethers such as diethylene glycol monoethyl ether and 3-methoxy-1-butanol; ketones such as methyl ethyl ketone; esters such as methyl heptanoate; and aliphatic and aromatic hydrocarbons such as toluene.

In forming lenses or other biomedical devices, the monomeric mixtures may be charged to a mold, and then subjected to heat and/or light radiation, such as ultraviolet (UV) radiation, to effect curing, or free radical polymerization, of the monomer mixture in the mold. Various processes are known for curing a monomeric mixture in the production of contact lenses or other biomedical devices, including spincasting and static casting. Spincasting methods involve charging the monomer mixture to a mold, and spinning the mold in a controlled manner while exposing the monomer mixture to light. Static casting methods involve charging the monomer mixture between two mold sections forming a mold cavity providing a desired article shape, and curing the monomer mixture by exposure to heat and/or light. In the case of contact lenses, one mold section is shaped to form the anterior lens surface and the other mold section is shaped to form the posterior lens surface. If desired, curing of the monomeric mixture in the mold may be followed by a machining operation in order to provide a contact lens or article having a desired final configuration. Such methods are described in U.S. Pat. Nos. 3,408,429, 3,660,545, 4,113,224, 4,197,266, 5,271,875, and 5,260,000. Additionally, the monomer mixtures may be cast in the shape of rods or buttons, which are then lathe cut into a desired shape, for example, into a lens-shaped article.

The contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be tamed over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

In the examples, the following abbreviations are used.
TRIS: 3-methacryloxypropyltris(trimethylsiloxy)silane
DMA: N,N-dimethylacrylamide
HEMA: 2-hydroxyethyl methacrylate
NVP: N-vinyl-2-pyrrolidone
HEMAVC: methacryloxyethyl vinyl carbonate
EGDMA: Ethylene glycol dimethacrylate
IBOMA: Isobornenyl methacrylate
D1173: 2-hydroxy-2-methyl-1-phenylpropan-1-one (available as Darocur 1173 initiator)
Vazo™ 64: azo bis-isobutylnitrile (AIBN)
IMVT: 1,4-bis(4-(2-methacryloxyethyl)phenylamino)anthraquinone

EXAMPLE 1

Preparation of a Cationic Polyurethane-Siloxane Prepolymer.

Into a dry, 1-L round bottom flask equipped with a condenser, under the flashing of dry nitrogen, was charged cationic silicone Silquat® DI-50 (available from Siltech, Inc) (60.48 g), IPDI (4.988 g), methylene chloride (200 mL) and dibutyltin dilaurate (0.215 g). The reaction mixture was heated to reflux under a nitrogen blanket. After 19 hours, an aliquot was taken, solvent removed and the amount of isocyanate remaining was determined to be 11.6% by titration. Methylene chloride (150 mL) was added to dilute the viscous solution. The contents of the solution were cooled to ambient temperature. HEMA (0.812 g) and 1,1'-bi-naphthol (10 mg) were then added and the contents were stirred at ambient until the isocyanate peak at 2250 $cm^{-1}$ disappeared from IR spectrum of the product (about 72 hours). The solvent was then removed and 60 g of prepolymer product was recovered.

EXAMPLE 2

Preparation of a Cationic Polyurethane Siloxane Prepolymer.

Into a dry, 1-L round bottom flask equipped with a condenser, under the flashing of dry nitrogen, was charged cationic silicone Silquat® DI-50 (157.95 g), IPDI (13.858 g), methylene chloride (300 mL) and dibutyltin dilaurate (0.470 g). The reaction mixture was heated to reflux under a nitrogen blanket. After 19 hours, an aliquot was taken, solvent removed and the amount of isocyanate remaining was determined to be 2.5% by titration. The contents of the solution were cooled to ambient temperature. HEMA (1.626 g) and 1,1'-bi-naphthol (24.6 mg) were added and the reaction was allowed to proceed until no isocyanate remained. The product was then recovered.

EXAMPLES 3-11

Preparation of Silicone Hydrogel Films.

Monomer mixtures were made by mixing the following components, listed in Tables 1 and 2 at amounts per weight: prepolymers of Examples 1 and 2; methacryloxypropyl tris (trimethylsiloxy)silane (TRIS); N,N-dimethylacrylamide (DMA); 2-hydroxy ethyl methacrylate (HEMA); N-vinyl pyrrolidone (NVP); and methacryloxyethyl vinylcarbonate (HemaVC). Additionally, each monomer mixture included: 1,4-bis(2-methacrylamidoethylamino)anthraquinone as a tint (150 ppm); hexanol as a diluent (10 parts by weight); and Darocur-1173™ UV initiator (Ciba Specialty Chemical, Ardsley N.Y.) (0.5 wt %) or Vazo™ 64 (a thermal polymerization initiator, said to be 2,2'-azobisisobutyronitrile, DuPont Chemicals, Wilmington, Del.).

The monomer mixtures were cast and cured into films. The mixture of Example 3 was cured under UV for 1 hour while the mixtures of Examples 4-11 were cured under the following thermal conditions: held at room temperature for 12 minutes, then ramped up to 100° C. in 54 minutes, and further held at 100° C. for 2 hours. Each monomer mixture was cast between three sets of glass plates, each set of plates separated by Teflon™ polymer tapes of different thicknesses, such that three sets of film samples were obtained for each monomer mixture, with film thicknesses of about 200, 400 and 600 microns. The cured films were then extracted with isopropanol overnight, followed by hydration in deionized (DI) water, boiled in DI water for 4 hours and then saturated in borate buffered saline or phosphate buffered saline to give hydrogel films. The water content was measured gravimetrically. Tensile Modulus and % elongation were conducted in borate buffered saline according to ASTM D-1708a, discussed above. Tear strengths were measured according to ASTM D-1938 under the same physical conditions as for tensile modulus. The oxygen permeabilities, reported in Dk (or barrer) units, were measured in phosphate buffered saline at 35° C., using acceptable films with three different thicknesses, as discussed above. For mechanical tests, films of around 200 microns were cast. For oxygen permeability tests, films with multiple thickness including 200 microns were cast.

TABLE 1

| | EXAMPLE | | | | |
|---|---|---|---|---|---|
| | 3 | 4 | 5 | 6 | 7 |
| Cationic Prepolymer Ex 1 | 36.4 | 32 | 60 | 60 | 60 |
| Cationic Prepolymer Ex 2 | | | | | |
| TRIS | 9.1 | 8 | 20 | 15 | 15 |
| DMA | 4.2 | 3.7 | 0 | 0 | 0 |
| NVP | 13.4 | 25.8 | 20 | 29 | 29 |
| HEMA | 1.5 | 1.3 | 20 | 2.5 | 2.5 |
| HEMAVC | 0.4 | 0.5 | 1 | 1 | 1 |
| IBOMA | | | | | 10 |
| h-hexanol | 34.6 | | | | |
| 3-Methoxy-1-Butanol | | 27.8 | 30 | 49 | 40 |
| Darocur-1173 | 0.3 | | | | |
| Vazo-64 | | 0.3 | 0.5 | 0.5 | 0.5 |
| IMVT | 150 ppm | 150 ppm | 0 | 150 ppm | 150 ppm |

TABLE 1-continued

| | EXAMPLE | | | | |
|---|---|---|---|---|---|
| | 3 | 4 | 5 | 6 | 7 |
| Properties | | | | | |
| % water | 54.8 | 61.4 | 34.1 | 48.3 | 38.9 |
| Modulus (g/mm$^2$) | 17 | 35 | 96 | 47 | 187 |
| % elongation | 100 | 53 | 88 | 91 | 91 |
| Tear (g/mm) | 1 | 0.5 | 2 | 2 | 5 |
| DK (barrer) | 142 | 69 | 82 | 156 | 122 |

TABLE 2

| | EXAMPLE | | | |
|---|---|---|---|---|
| | 8 | 9 | 10 | 11 |
| Cationic Prepolymer Ex 1 | 60 | | | |
| Cationic Prepolymer Ex 2 | | 60 | 60 | 60 |
| TRIS | 15 | 15 | 15 | 15 |
| NVP | 29 | 22 | 27 | 29 |
| HEMA | 2.5 | 10 | 5 | 2.5 |
| HEMAVC | 1 | 0.8 | 0.9 | 0.9 |
| EGDMA | | 0.4 | 0.4 | 0.4 |
| IBOMA | 4 | 4 | 4 | 4 |
| 3-Methoxy-1-Butanol | 40 | 10 | 10 | 10 |
| Vazo-64 | 0.5 | 0.6 | 0.6 | 0.6 |
| IMVT | 150 ppm | 150 ppm | 150 ppm | 150 ppm |
| Properties | | | | |
| % water | 47.2 | 39.8 | 40.5 | 43.9 |
| Modulus (g/mm$^2$) | 45 | 87 | 69 | 56 |
| % elongation | 120 | 73 | 60 | 41 |
| Tear (g/mm) | 3 | 3 | 2 | 2 |
| DK (barrer) | 149 | 117 | 133 | 120 |

The oxygen permeabilities of these hydrogels having a water content between about 40 to 55% were at least 110 up to 156 DK, which were much higher than those of typical non-ionic silicone hydrogels. Normally, silicone hydrogels having these water contents were less than 90 DK. Therefore, by employing a cationic prepolymer of this invention, it was possible to obtain silicone hydrogels with unusually super high oxygen permeability

EXAMPLE 12

Preparation of Methacrylate-Capped Prepolymer of Cationic Silicone by Reacting with Isocyantoethyl Methacrylate.

Silquat® DI-50 (66.66 g solution in THF) was placed in a preweighed 3-neck, 500 mL round bottom flask and added with 150 mL of cyclohexane. The mixture was azeotropically distilled using a Dean Stock trap to collect distillate. After 5 hours, most of the solvent was removed and the residue became viscous (weighed 47.09 g, M$_n$ was about 3,860 (0.01145 mole)). Under a nitrogen blanket, anhydrous methylene chloride (50 mL), 1,1'-bis-2-naphthol (0.009 g), stannous octoate (0.1427 g) and diazabicyclic octane (DABCO) (0.1601 g) were added to the flask. The contents were allowed to dissolve at 30-40° C. Next, isocyanatoethyl methacrylate (4.5725 g, 0.02698 mole, or 14% excess) was added and stirred for 48 hours at 36° C. The reaction product was analyzed by MALDI (Model: Voyager-DE STR) to determine if the starting material had been capped with isocyanatoethyl methacrylate. It was determined that the reaction products were IEM-capped. The product was then recovered.

EXAMPLE 13

Preparation of Silicone Hydrogel Lenses.

A monomer mixture was made by mixing the following components, listed in Table 3 at amounts per weight. The mixture was found clear before adding the blue tint.

TABLE 3

| Ingredient | Amount |
| --- | --- |
| Cationic Prepolymer Ex 12 | 9.3 (1.1451 g) |
| TRIS | 23.25 (2.8638 g) |
| NVP | 41.85 (5.1530 g) |
| HEMA | 18.6 (2.2924 g) |
| 1,2 propanol | 5 (0.6124 g) |
| UV blocker | 1.5 (0.1841 g) |
| Vazo-64 | 0.5 (0.061 g) |
| Reactive blue tint | 0.0012 g |

Lenses were cast using polypropylene molds, both in an open air bench top and in a dry box filled with nitrogen, and then cured in an oven at under the following thermal conditions: held at room temperature for 12 minutes, then ramped up to 100° C. in 54 minutes, and further held at 100° C. for 2 hours. After casting, the lenses were released from the molds and extracted in isopropanol (IPA) for 60 minutes.

For lenses cast in air, the following results were obtained: extractable 11.6%, and water content 49.2 weight %. For lenses cast in a dry box, the following results were obtained: extractable 11.2%, and water content 48.7 weight %. The extracted lenses were autoclaved in borate buffered saline and were clear. The lenses thus obtained had a modulus of 137 $g/mm^2$.

EXAMPLE 14

Preparation of Methacrylate-Capped Prepolymer of Cationic Silicone by Reacting with Methacryloyl Chloride.

Following the same procedure as in Example 12, Silquat® DI-50 (61.7 g) was dried by azeotropic distillation with cyclohexane, to provide 45.01 g (0.01166 mole) of dried product ($M_n$=3,860). Under a nitrogen blanket, anhydrous methylene chloride (180 mL) was added to the flask and then refluxed overnight. Based on MALDI, no reaction took place. Next, 4-dimethylamino pyridine (3.6 g) was added. A slight exothermic was then observed and the color of the mixture changed from clear to red. After the mixture was refluxed overnight, anhydrous methanol (6 g) was added and stirred for 5 hours. No acid chloride was found by IR. MALDI indicated that most precuts were mono-methacrylated. The product mixture was then added with more methylene chloride and extracted with 50 mL of water. The organic layer was separated, dried and the product was recovered.

EXAMPLE 15

Preparation of Silicone Hydrogel Lenses.

A monomer mixture was made by mixing the following components, listed in Table 4 at amounts per weight.

TABLE 4

| Ingredient | Amount |
| --- | --- |
| Cationic Prepolymer Ex 14 | 9.56 (0.9681 g) |
| TRIS | 23.07 (2.33 g) |
| NVP | 41.74 (4.2252 g) |
| HEMA | 18.56 (1.879 g) |
| 1,2 propanol | 5.06 (0.5127 g) |
| UV blocker | 1.55 (0.1574 g) |
| Vazo-64 | 0.5 (0.0506 g) |
| Properties | |
| % water | 63.7 |
| Modulus (g/mm$^2$) | 40 ± 2 |
| % elongation | 249 +/− 16 |
| Tear (g/mm) | 6 |
| DK (barrer) | 40 |

The monomer mixture was cast between silane-treated glass plates and cured under heat using the following conditions: held at room temperature for 12 minutes, then ramped up to 100° C. in 54 minutes, and further held at 100° C. for 2 hours. The lenses were released from the glass plates, extracted with IPA for 1.5 hours and hydrated in a borate buffered saline. Extractables: 16.6%.

EXAMPLE 16

Preparation of Methacrylate-Capped Prepolymer of Cationic Silicone by Reacting with Methacryloyl Chloride.

The preparation of the prepolymer described in Example 14 was repeated in essentially the same manner. Silquat® DI-50 (63.69 g in THF) was dried by azeotropic distillation with cyclohexane, to obtain 46.77 g of dried product. Under a nitrogen blanket, anhydrous methylene chloride (170 mL), methacryloyl chloride (3.3 g), triethylamine (5 mL), and 4-N-dimethylaminopyridine (0.06 g) were added to the flask. The mixture was refluxed for 2 days, and MALDI analyses indicated most of the product was difunctionalized with very little mono functionalized and starting material remaining. The product solution was extracted with water. After separation, the organic layer was dried and stripped under vacuum to remove solvent to recover the product.

EXAMPLE 17

Preparation of a Silicone Hydrogel Film.

A monomer mixture was made by mixing the following components, listed in Table 5.

TABLE 5

| Ingredient | Amount |
| --- | --- |
| Cationic Prepolymer Ex 16 | 202999 g |
| TRIS | 5.7519 g |
| NVP | 10.3482 g |
| HEMA | 4.6029 g |
| 1,2 propanol | 1.234 g |
| UV blocker | 0.3722 g |
| Vazo-64 | 0.12 g |
| Properties | |
| % water | 51 |
| Modulus (g/mm$^2$) | 105 |
| Tear (g/mm) | 4 |
| DK (barrer) | 32 |

The monomeric mixture was cast between silane-treated glass plates to obtain films with 3 different thickness of roughly 200, 400 and 600 microns and cured under the following thermal conditions: held at room temperature for 12 minutes, then ramped up to 100° C. in 54 minutes, and further held at 100° C. for 2 hours. The films were then released from the glass plates, extracted with IPA for 3 hours and hydrated in DI water.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A prepolymer comprising at least one block of Formula II and terminated with a polymerizable ethylenically unsaturated radical:

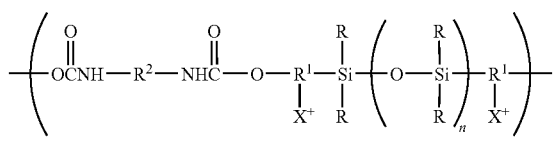

(II)

wherein n is at least 1, R is independently a monovalent hydrocarbon radical having 1 to 30 carbon atoms which may include ether linkages therebetween or a halogen substituted monovalent hydrocarbon radical having 1 to 20 carbon atoms which may include ether linkages therebetween, a $C_1$-$C_{20}$ ester group, an ether or polyether-containing group, an ureido group, an amide group, an amine group, a substituted or unsubstituted $C_1$-$C_{30}$ alkoxy group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, fluorine or a vinyl group, $R^1$ is independently a substituted or unsubstituted divalent hydrocarbon radical having 1 to 30 carbon atoms which may include ether linkages therebetween, $X^+$ is independently a cationic-containing group and $R^2$ is a diradical residue of a diisocyanate.

2. The prepolymer of claim 1, wherein $X^+$ is independently a cationic group comprising an ammonium, phosphonium or sulphonium cationic-containing group.

3. The prepolymer of claim 1, wherein $R^1$ is a $C_1$-$C_{12}$ alkylene group optionally substituted with an ether linkage.

4. The prepolymer of claim 1, wherein R is a $C_1$-$C_6$ alkyl group.

5. The prepolymer of claim 1, wherein the prepolymer is terminated at two ends with a polymerizable ethylenically unsaturated radical.

6. The prepolymer of claim 1, wherein the polymerizable ethylenically unsaturated radical is of the formula

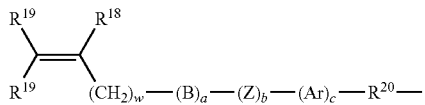

wherein $R^{18}$ is hydrogen or methyl; $R^{19}$ is independently hydrogen, an alkyl radical having 1 to 6 carbon atoms, or a —CO—Y—$R^{21}$ radical wherein Y is —O—, —S— or —NH— and $R^{21}$ is a divalent alkylene radical having 1 to about 10 carbon atoms; $R^{20}$ is an alkyl radical having 1 to about 12 carbon atoms; B denotes —O— or —NH—; Z denotes —CO—, —OCO— or —COO; Ar denotes an aromatic radical having 6 to about 30 carbon atoms; w is 0 to 6; a is 0 or 1; b is 0 or 1; and c is 0 or 1.

7. The prepolymer of claim 1, which is of Formula III:

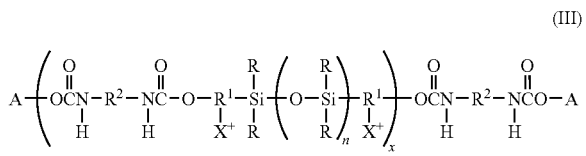

(III)

wherein n, R, $R^1$, $R^2$ and $X^+$ have the aforestated meanings; x is at least about 1 and each A is independently a polymerizable ethylenically unsaturated radical.

8. The prepolymer of claim 7, wherein each A is independently a polymerizable ethylenically unsaturated radical of the formula

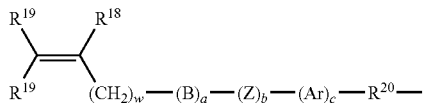

wherein
$R^{18}$ is hydrogen or methyl;
$R^{19}$ is independently hydrogen, an alkyl radical having 1 to 6 carbon atoms, or a —CO—Y—
$R^{21}$ radical wherein Y is —O—, —S— or —NH— and $R^{21}$ is a divalent alkylene radical having 1 to about 10 carbon atoms;
$R^{20}$ is an alkyl radical having 1 to about 12 carbon atoms;
B denotes —O— or —NH—; Z denotes —CO—, —OCO— or —COO;
Ar denotes an aromatic radical having 6 to about 30 carbon atoms;
w is 0 to 6; a is 0 or 1; b is 0 or 1; and c is 0 or 1.

9. The prepolymer of claim 7, wherein x is from 1 to about 20.

10. A copolymer comprising a polymerization product of a monomeric mixture comprising one or more of the prepolymers of claim 7.

11. The copolymer of claim 10, wherein the monomeric mixture further comprises a hydrophilic monomer, hydrophobic monomer or both.

12. The copolymer of claim 11, wherein the hydrophilic monomer is selected from the group consisting of 2-hydroxyethylmethacrylate, 2-hydroxyethylacrylate, glyceryl methacrylate; N-vinyl pyrrolidone; N-vinyl-N-methyl acetamide, N,N-dimethyl methacrylamide, N,N-dimethylacrylamide, acrylic acid, methacrylic acid and mixtures thereof.

13. The copolymer of claim 11, wherein the hydrophobic monomer is a silicone-containing monomer having from 1 to about 20 silicon atoms.

14. The copolymer of claim 13, wherein the silicone monomer is 3-methacryloxypropyl tris(trimethylsiloxy)silane.

15. The copolymer of claim 11, wherein the hydrophobic monomer is an aliphatic ring containing monomer selected from the group consisting of isobornyl acrylate, iosbomyl methacrylate, cyclohexyl acrylate, cyclohexyl methacrylate and combinations thereof.

16. The copolymer of claim 10, having:
a water content of about 30 weight percent and an oxygen permeability greater than about 80 barrers.

17. The copolymer of claim 10, having:
a water content of about 30 to about 60 weight percent, and an oxygen permeability greater than about 110 barrers.

18. A biomedical device comprising a copolymer of claim 10.

19. An ophthalmic lens comprising a copolymer of claim 10.

20. A contact lens comprising a copolymer of claim 10.

21. A hydrogel comprising a hydrated polymerization product of a monomeric mixture comprising one or more of the prepolymers of claim 7.

22. The hydrogel of claim 21, wherein the monomeric mixture further comprises a comonomer.

23. The hydrogel of claim 21, wherein the monomeric mixture further comprises at least one hydrophilic comonomer selected from the group consisting of an unsaturated carboxylic acid, (meth)acrylic substituted alcohol, vinyl lactam, (meth)acrylamide and combinations thereof.

24. A copolymer comprising a polymerization product of a monomeric mixture comprising one or more of the prepolymers of claim 1.

25. The copolymer of claim 24, wherein the monomeric mixture further comprises a hydrophilic monomer, hydrophobic monomer or both.

26. The copolymer of claim 25, wherein the hydrophilic monomer is selected from the group consisting of 2-hydroxyethylmethacrylate, 2-hydroxyethylacrylate, glyceryl methacrylate; N-vinyl pyrrolidone; N-vinyl-N-methyl acetamide, N,N-dimethyl methacrylamide, N,N-dimethylacrylamide, acrylic acid, methacrylic acid and combinations thereof.

27. The copolymer of claim 25, wherein the hydrophobic monomer is a silicone-containing monomer having from 1 to about 20 silicon atoms.

28. The copolymer of claim 27, wherein the silicone monomer is 3-methacryloxypropyl tris(trimethylsiloxy)silane.

29. The copolymer of claim 25, wherein the hydrophobic monomer is an aliphatic ring containing monomer selected from the group consisting of isobornyl acrylate, isobornyl methacrylate, cyclohexyl acrylate, cyclohexyl methacrylate and combinations thereof.

30. The copolymer of claim 24, having:
a water content of about 30 weight percent and an oxygen permeability greater than about 80 barrers.

31. The copolymer of claim 24, having:
a water content of about 30 to about 60 weight percent, and an oxygen permeability greater than about 110 barrers.

32. A biomedical device comprising a copolymer of claim 24.

33. An ophthalmic lens comprising a copolymer of claim 24.

34. A contact lens comprising a copolymer of claim 24.

35. A hydrogel comprising a hydrated polymerization product of a monomeric mixture comprising one or more of the prepolymers of claim 1.

36. The hydrogel of claim 35, wherein the monomeric mixture further comprises a comonomer.

37. The hydrogel of claim 35, wherein the monomeric mixture further comprises at least one hydrophilic comonomer selected from the group consisting of an unsaturated carboxylic acid, (meth)acrylic substituted alcohol, vinyl lactam, (meth)acrylamide and combinations thereof.

38. A prepolymer of Formula IV:

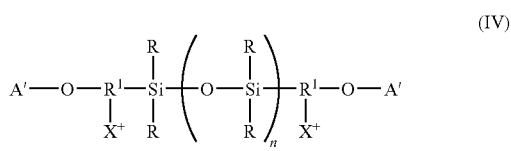

wherein n is at least 1, R is independently hydrogen, a monovalent hydrocarbon radical having 1 to 30 carbon atoms which may include ether linkages therebetween or a halogen substituted monovalent hydrocarbon radicals having 1 to 20 carbon atoms which may include ether linkages therebetween, a $C_1$-$C_{20}$ ester group, an ether or polyether-containing group, an ureido group, an amide group, an amine group, a substituted or unsubstituted $C_1$-$C_{30}$ alkoxy group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, fluorine or a vinyl group, $R^1$ is independently a substituted or unsubstituted divalent hydrocarbon radical having 1 to 30 carbon atoms which may include ether linkages therebetween, $X^+$ is independently a cationic group; and each A' is independently a polymerizable ethylenically unsaturated organic-containing radical.

39. The prepolymer of claim 38, wherein $X^+$ is independently a cationic group comprising an ammonium, phosphonium or sulphonium cationic group.

40. The prepolymer of claim 38, wherein each A' is an isocyanate ethyl methacrylate-containing radical.

41. A copolymer comprising a polymerization product of a monomeric mixture comprising one or more of the prepolymers of claim 38.

42. A biomedical device comprising a copolymer of claim 41.

43. An ophthalmic lens comprising a copolymer of claim 41.

44. A contact lens comprising a copolymer of claim 41.

45. The copolymer of claim 41, wherein the monomeric mixture further comprises a hydrophilic monomer, hydrophobic monomer or both.

46. The copolymer of claim 45, wherein the hydrophilic monomer is selected from the group consisting of 2-hydroxyethylmethacrylate, 2-hydroxyethylacrylate, glyceryl methacrylate; N-vinyl pyrrolidone; N-vinyl-N-methyl acetamide, N,N-dimethyl methacrylamide, N,N-dimethylacrylamide, acrylic acid, methacrylic acid and combinations thereof.

47. The copolymer of claim 45, wherein the hydrophobic monomer is a silicone-containing monomer having from 1 to about 20 silicon atoms.

48. The copolymer of claim 47, wherein the silicone monomer is 3-methacryloxypropyl tris(trimethylsiloxy)silane.

49. The copolymer of claim 45, wherein the hydrophobic monomer is an aliphatic ring containing monomer selected from the group consisting of isobornyl acrylate, isobornyl methacrylate, cyclohexyl acrylate, cyclohexyl methacrylate and combinations thereof.

50. A hydrogel comprising a hydrated polymerization product of a monomeric mixture comprising one or more of the prepolymers of claim 38.

51. The hydrogel of claim 50, wherein the monomeric mixture further comprises a comonomer.

52. The hydrogel of claim 50, wherein the monomeric mixture further comprises at least one hydrophilic comonomer selected from the group consisting of an unsaturated carboxylic acid, (meth)acrylic substituted alcohol, vinyl lactam, (meth)acrylamide and combinations thereof.

* * * * *